United States Patent
Amoah (10) Patent No.: US 10,245,106 B2
(45) Date of Patent: Apr. 2, 2019

(54) LAPAROSCOPIC INSTRUMENTS (71) Applicant: Francis Kweku Egyin Amoah, Reading (GB)

(72) Inventor: Francis Kweku Egyin Amoah, Reading (GB)

(73) Assignee: ASALUS MEDICAL INSTRUMENTS LIMITED, Cardiff (GB)

( * ) Notice: Subject to any disclaimer, the term of this patent is extended or adjusted under 35 U.S.C. 154(b) by 0 days.

(21) Appl. No.: 14/356,333

(22) PCT Filed: Oct. 31, 2012

(86) PCT No.: PCT/GB2012/052707
§ 371 (c)(1),
(2) Date: May 5, 2014

(87) PCT Pub. No.: WO2013/068724
PCT Pub. Date: May 16, 2013

(65) Prior Publication Data
US 2014/0303615 A1 Oct. 9, 2014

(30) Foreign Application Priority Data

Nov. 7, 2011 (GB) .................................. 1119134.3

(51) Int. Cl.
*A61B 18/18* (2006.01)
*B03C 3/68* (2006.01)
(Continued)

(52) U.S. Cl.
CPC .......... *A61B 18/18* (2013.01); *A61B 18/1233* (2013.01); *B03C 3/38* (2013.01);
(Continued)

(58) Field of Classification Search
CPC .................................................. A61B 18/1233
See application file for complete search history.

(56) References Cited

U.S. PATENT DOCUMENTS 3,838,684 A * 10/1974 Manuel .............. A61B 5/02438
361/283.4
4,745,520 A * 5/1988 Hughey ................. H02H 7/003
118/621
(Continued)

FOREIGN PATENT DOCUMENTS

EP 0558318 A2 9/1993
EP 1776929 A1 4/2007
(Continued)

Primary Examiner — Luther G Behringer
(74) Attorney, Agent, or Firm — King & Schickli, PLLC (57) ABSTRACT A DC driven ionization apparatus is provided for ionizing a local atmosphere in which a corporeal surgical or cosmetic procedure is to be performed, the ionization apparatus including a safety circuit comprising detector means for detecting when a hazard condition exists, such as a short circuit or high charge level condition, a circuit controller for actuating switch means to turn the DC supply off and thereafter to cyclically reconnect and disconnect the DC supply until the hazard condition has been rectified, and re-set means for thereafter re-setting a continuous DC supply to the circuit until the next occurrence of a hazard condition or until the procedure is complete.

20 Claims, 7 Drawing Sheets (51) Int. Cl.
*A61B 18/12* (2006.01)
*B03C 3/38* (2006.01)
*A61B 18/00* (2006.01)

(52) U.S. Cl.
CPC ...... *B03C 3/68* (2013.01); *A61B 2018/00827* (2013.01); *A61B 2018/1266* (2013.01); *A61B 2218/008* (2013.01); *B03C 2201/26* (2013.01)

(56) References Cited

U.S. PATENT DOCUMENTS

| | | | | |
|---|---|---|---|---|
| 4,781,175 A | * | 11/1988 | McGreevy | A61B 18/042 219/121.5 |
| 4,951,672 A | * | 8/1990 | Buchwald | A61B 5/0428 128/901 |
| 6,296,636 B1 | * | 10/2001 | Cheng et al. | 606/32 |
| 2003/0187430 A1 | | 10/2003 | Vorisek | |
| 2005/0177150 A1 | * | 8/2005 | Amoah | A61B 18/1206 606/34 |
| 2007/0093801 A1 | * | 4/2007 | Behnke | A61B 18/1233 606/34 |
| 2007/0161979 A1 | * | 7/2007 | McPherson | A61B 18/1233 606/35 |
| 2008/0001608 A1 | * | 1/2008 | Saulnier | A61B 5/0536 324/601 |
| 2009/0248022 A1 | * | 10/2009 | Falkenstein | A61B 18/1442 606/51 |

FOREIGN PATENT DOCUMENTS

| | | |
|---|---|---|
| EP | 1810631 A2 | 7/2007 |
| JP | S62133947 A | 6/1987 |
| JP | 2001520081 A | 10/2001 |
| JP | 2002538881 A | 11/2002 |
| JP | 2006288553 A | 10/2006 |
| RU | 2009606 C1 | 3/1994 |
| RU | 2007138008 A | 4/2009 |
| WO | 2004062516 A1 | 7/2004 |
| WO | 2006059067 A1 | 6/2006 |
| WO | 2011010148 A2 | 1/2011 |

* cited by examiner

LAPAROSCOPIC INSTRUMENTS

FIELD OF THE INVENTION

This invention relates to laparoscopic instruments such as ionisation instruments of the type described in WO2011/010148.

BACKGROUND OF THE INVENTION

Laparoscopic, or "keyhole" surgery involves a surgeon performing a surgical procedure on a patient using instruments that are inserted into the body, but which are manipulated using hand/robotic controls located externally of the patient. The surgeon usually sees what is happening by using an endoscope which is inserted at or near the operation site and in order to gain access to the operation site and to provide space for the instruments, a cavity is usually opened up within the patient's body by inflation using a suitably inert gas, such as $CO_2$.

Many laparoscopic procedures involve the use of thermal cutting instruments, such as lasers and diathermy devices, which can cut and cauterise tissues by ablation, heating, freezing and the like. In certain situations, the surgeon's view can be become obscured by smoke, vapours or other aerosols and it is therefore often necessary to provide means for extracting the smoke, vapours or aerosols from the operation site. The extraction of smoke, vapours and aerosols can be achieved in a number of ways, such as by over-pressurising the cavity and providing a gas bleed tube fitted with a filter.

SUMMARY OF THE INVENTION

This invention is particularly concerned with smoke/vapour removal via ionisation in the manner as described in WO2011/010148, the disclosure of which is incorporated herein by reference, which involves inserting an ionising electrode disposed at the end of an insulated rod or "wand", into the operation site, which electrode is maintained at an electrical potential with respect to the patient's body so that the smoke/vapour particles/droplets in the air become ionised and are attracted to the patient's body. The smoke/vapour is thus removed from the surrounding atmosphere and transferred to a surface where it can thereafter be removed periodically by washing etc.

When using such an ionising electrode, precautions must be taken to ensure that electrical contact is not made between the electrode and other surgical instruments within the cavity, which could lead to instrument failure or short-circuiting, and that hazardous electric charge levels do not build-up within the patient, which have the potential to cause atrial fibrillation (AF), if neglected. In addition, any electrical devices connected to patients must satisfy rigorous safety standards to ensure that interference between different devices is minimised such that the risks of electric shock and harm to the patient are minimised.

The present invention is derived from the realisation that, unlike surgical instruments that couple low voltage DC or reversing polarity, AC waveforms, to a patient, surgical instruments or devices that couple high voltage DC waveforms to the patient are capable of storing electrical charge either directly or indirectly, such as by storing electrical charge within the instrument or within the corporeal body on which a procedure is to be performed in much the same manner as a capacitor stores electrical charge, with the consequence that because of the electrical potential difference between the charged instrument or corporeal body and the ground there is a risk of unwanted electrical discharge.

According to the invention, there is provided DC driven ionisation apparatus for ionising a local atmosphere in which a corporeal surgical or cosmetic procedure is to be performed, the ionisation apparatus including a safety circuit comprising detector means for detecting when a hazard condition exists, such as a short circuit or high charge level condition, a circuit controller for actuating switch means to turn the DC supply off and thereafter to cyclically reconnect and disconnect the DC supply until the hazard condition has been rectified, and re-set means for thereafter re-setting a continuous DC supply to the circuit until the next occurrence of a hazard condition or until the procedure is complete.

With this arrangement accidental damage to surgical instruments due to them inadvertently coming into contact with the ionising discharge electrode can be obviated by immediate interruption of the high voltage DC supply for a duration sufficient for the cause of the short circuit to be found and rectified, such as by the surgeon moving a surgical instrument away from the ionising electrode. Similarly, where the hazard condition detected is the build up of an unacceptably high level of electrical charge, which may be due to a number of reasons including a cumulative build-up of capacitance in the corporeal body or in surgical instruments and associated cabling, immediate action can be taken by disconnecting the DC power supply and monitoring the charge within the system until it falls below a required maximum safe level.

Conveniently, the safety circuit includes a network of high voltage resistors coupled to the DC supply, which circuit may include two or more series-wired resistors for limiting current output, one or more current sensing resistors for enabling the level of current to be sensed, one or more shunt resistors which are arranged to consume a signature level load and thus provide an assurance of the integrity of the safety monitoring controls. The safety circuit further comprises one or more series-wired resistors at or near the output electrode of the ionisation apparatus, which may be two or more orders of magnitude less than the impedance of the series-wired resistors so as to have no significant impact on the functional efficacy of the ioniser but being able to prevent or inhibit discharge of charge stored between the output electrode and the return electrode of the ionisation apparatus.

Using the foregoing concepts, high voltage DC current can be coupled to a patient via series-wired resistors having a cumulative value relative to the applied voltage resulting in a maximum possible current of typically, between 5 and 50 µA and preferably between 10 to 50 µA, with resistors being placed in both the output and return connections. Additionally, active control of current to limit it to a maximum of 10 µA may be used to maximise particle clearing at lower output electrode impedances by combining the use of the active current limit and a resistive current limit where the relationship between the high voltage and the combined resistance provides a current limit of between 20 and 50 µA.

The invention also provides a means for responding to excessively low output electrode impedances by cyclically interrupting the output voltage and through the use of a resistor placed near to the moveable wand and the output electrode so as to avoid unwanted electrical discharge when the output electrode is close to patient tissue and which would otherwise be perceived by the user of the wand.

The invention also extends to the concept of linking the activation of the ionisation apparatus with the activation of particle-producing surgical instruments, such as by the use of commonly-wired foot switches, wireless signalling from the particle producing surgical instrument or detection of signature radio frequency emissions in the case of electro-surgical instruments being used.

BRIEF DESCRIPTION OF THE DRAWING FIGURES

The invention will now be described, by way of example only, in which.

DETAILED DESCRIPTION OF THE INVENTION

Figure 1:
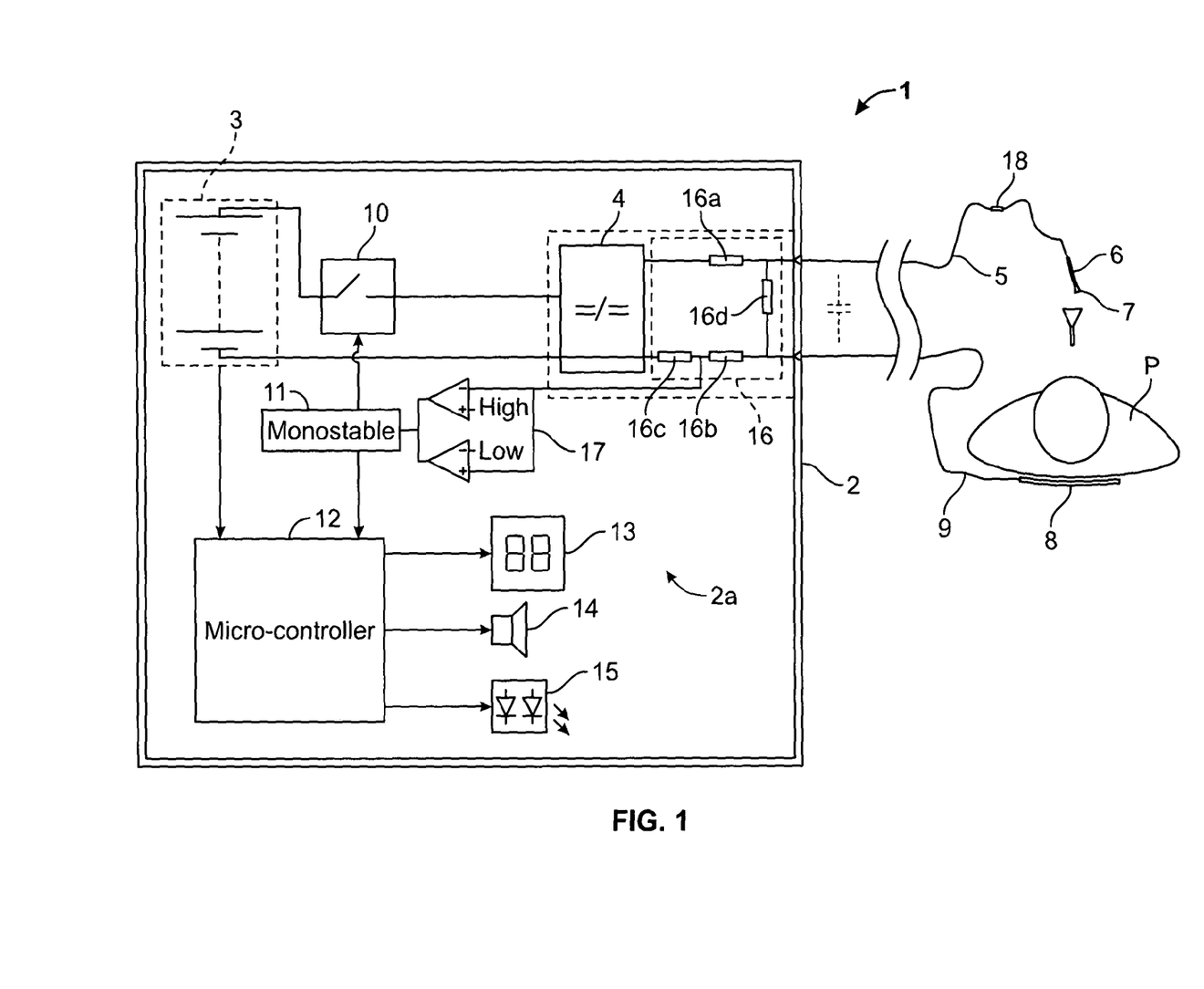
FIG. 1 is a schematic arrangement of an ionising apparatus according to a first embodiment.

Referring firstly to FIG. 1, ionising apparatus shown generally at 1 comprises an insulated housing 2 comprising safety circuitry 2a for operating the ionising apparatus 1. The safety circuit 2a comprises a DC power source battery 3 for powering a DC switch mode power supply DC to DC voltage converter 4 which steps up the voltage to approximately 10 kV to an active cable 5 on the free end of which is a non-conductive rod or wand 6 from which protrudes the free end of the active cable 5 in the form of an output electrode 7. A return electrode in the form of an electrically conductive pad 8 is connected to a return cable 9 to the battery 3, the electrodes 7 and 8 providing, in use, an ionisation path therebetween in the manner as described in WO2011/010148.

The housing 2 is sufficiently insulated so as to prevent the possibility of any significant electrical path being established with its surroundings and, indirectly, with a patient P, whilst still allowing the internal circuitry of the housing 2 to assume a voltage potential of up to the same order of magnitude as that applied to the patient P during the surgical procedure in which the ionising wand 6 is being used intra-corporeally such as e.g., during a laparoscopic procedure.

Referring now to the internal circuitry components, these include an isolation switch 10 for the converter 4, a monostable 11 for re-enabling the switch 10 and a micro-controller 12 coupled to user interfaces in the form of, respectively, a digital display 13, audio output speaker 14 and LEDs 15, which collectively advise the user of the apparatus 1 of the charge status of the battery 3 and other parameters concerning the status of the converter 4, active cable 5 and associated components connected thereto or therewith.

The output from the converter 4 is coupled to the active cable 5 and the return cable 9 via a high voltage resistor network shown generally in broken outline at 16. This comprises a pair of series wired resistors 16a, 16b close linked between 0.4 and 1.2 G Ohm, a series current sense resistor 16c of 3 to 5 orders of magnitude lower resistance, and a shunt resistor 16d in parallel across the active outward cable 5 and the return cable 9, typically having a resistance an order of magnitude greater than the accumulative resistance from the series connected resistors 16a, 16b and 16c.

The converter 4 and high voltage resistor network 16 is suitably encapsulated in an inert medium such as epoxy resin not prone to providing an ionising path that might otherwise bypass the effects of the resistor network 16.

Between the monostable 11 and the return cable 9, between resistors 16b and 16c, is a window comparator 17 which defines the acceptable limits of current for safe operation.

In accordance with the invention, multiple means are provided for limiting current output from the high voltage converter 4 to and from the patient P via the active cable 5 and return cable 9, the first being in the converter 4 itself which is appropriately limited by design to a maximum current of 30 μA of steady-state output current.

A second means of limiting current output is provided by the presence of the series-wired resistors 16a, 16b which rely on the converter 4 coupling a known maximum high voltage to the whole of the resistor network 16. This second limiting means is configured under low impedance conditions between the active cable 5 and associated wand 6 and the output electrode-return pad 8 and return cable 9 to provide instantaneous current limit of up to 10 μA, which limit is considered to present a negligible risk of causing interference with the cardiac sinus rhythm.

Where the safety circuit 2a for the ionisation apparatus comprises two or more resistors wired in series, a degree of protection is still available in the event that one fails with a low impedance. In such a situation, the patient current is limited to no more than, say, 20 μA, or less than 20 μA if more than 2 resistors are used in series. In accepted safety analysis methodology, the slight increase in risk of interference in patient sinus rhythm at 20 μA is factored down by the low probability of component failure, and so the combined likelihood of sinus rhythm interference remains negligible. In addition, it has also been found to be advantageous to place high impedances without which there would be a risk that high frequency current from third party devices such as electro-surgical systems would couple through the controls via stray capacitance to the immediate surroundings. This aim may conveniently be achieved by means of a suitably placed series-wired resistor 16b.

A third safety feature utilises the voltage across the current sense resistor 16 c which is required by the window comparator 17 to reside between a first, lower limit resulting from the current drawn from the minimum possible load, caused by the effect of the shunt resistor 16 d on the voltage Vhv from the converter 4, as applied to the resistor network 16, and a second, upper, limit reached at the lower of 10 μA and Vhv/(R16 a+R16 b) being the patient current level between the output and return electrodes 7, 8, where Vhv is the amplitude of the high voltage output from the DC to DC converter when no load current is being drawn. In the event of the current through the sense resistor 16 c falling outside the acceptable limits defined by the window comparator 17, the connection between the battery 3 and the converter 4 is broken by the isolation switch 10 for a duration defined by the monostable 11. Concurrent with this interruption, the monostable circuit 11 signals to the user interface micro controller 12 to provide an audio visual indication of the event via the display 13, speaker 14 and LED's 15.

The interruption duration can be between 0.2 to 10 seconds but is optimally between 2 and 3 seconds, this being considered long enough to allow the surgeon to respond to the hazard condition, which may have been caused by an inadvertent contact between the output electrode 7 and a third party instrument being used by the surgeon, or by an unacceptably close proximity to the patient corporeal tissue. Whatever the cause, at the end of the interruption the monostable 11 re-enables the isolating switch 10 and allows an attempt to re-establish an acceptable output current over a shorter period of time, such as 200 ms. This time is needed to allow expected stray capacitances in the high voltage circuit to be recharged by the output from the resistor network 16. These capacitances can be estimated to be of the order of 10 pF to 100 pF and so can take 0.1 to 0.5 seconds to recharge, depending on both the size of stray capacitance and the value of the series resistors 16a, 16b.

A useful feature of this timing arrangement is that where the over-current condition is caused by connection to large capacitances in patient connections from third party surgical equipment, a dramatic reduction in the rate of build up of uncontrolled charge is afforded. In the preferred embodiment, the output charge delivered into third party equipment capacitance can be reduced by a factor of about 10, compared to that delivered without the interruption of the isolator switch 10.

As an example of a capacitor hazard, a monopolar electrosurgical generator is allowed by medical device standards to couple to the patient via a 5 µF capacitor. Once charged to just a few volts, there is sufficient energy stored to cause involuntary motor nerve stimulation when the active electrode is next brought into contact with a muscle, which is seen as an undesirable twitch of the patient muscle during surgery. This improvement both provides an alarm to the surgeon while extending the time needed to reach such an undesirable level of third party capacitor charge from around 2 seconds to around 20 seconds.

A further refinement in user-perceived safety is achieved if a means is additionally provided to limit the peak displacement current that flows from the output electrode 7 when brought into abrupt electrical contact with patient tissue. This contact may be direct, or it may instead be in the form of air discharge or arcing of typically less than two millimeters in length between the first electrode 7 and patient tissue. Such a discharge is supported by the capacitance between the active cable 5 and the return cable 9, which may typically be between 10 pF to 100 pF, including items connected in common, such as the patient tissue bulk itself. Such unwanted electrical discharge can be prevented by the use of a series-wired resistor 18 between the proximal end of the wand 6 and the distal portion of the active cable 5 i.e. outside the housing 2. The placing of such a series-wired resistor 18, if of two or more orders of magnitude less than the impedance of the series output resistors 16a, 16b, has no significant impact on the functional efficacy of the ioniser 1, but can prevent the user-perceivable discharge of the charge stored between active cable 5 and the return cable 9, and in practice it has been found that a value of 1 MΩ for resistor 18 to be effective.

Figure 2:
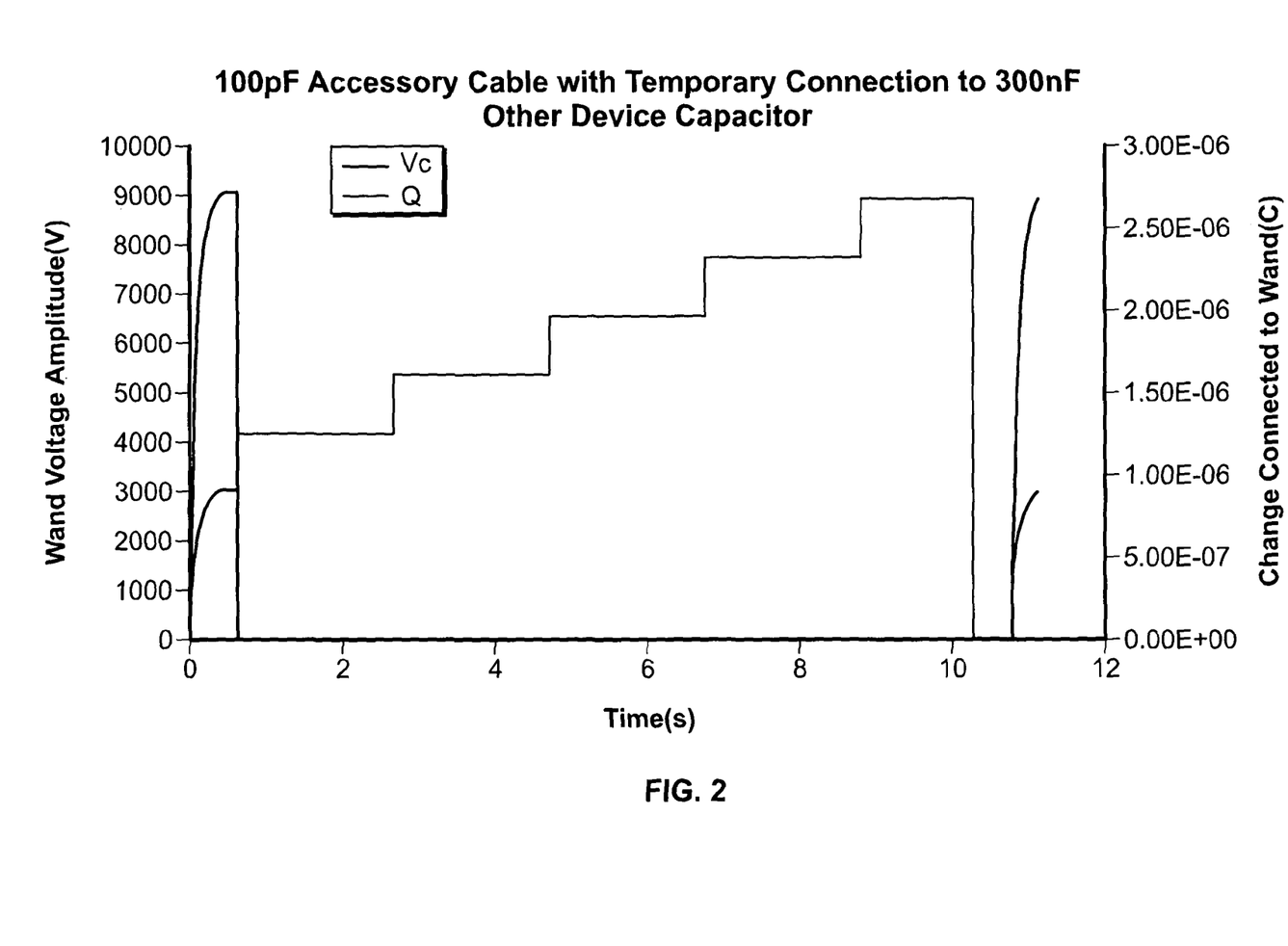
FIG. 2 is a graph showing a hypothetical short circuit hazard event while using the apparatus in FIG. 1.

Operation of the circuit shown in FIG. 1 is hypothetically represented in FIG. 2, which depicts a short-circuit event occurring 0.5 seconds into the cycle, analogous to e.g. a third party surgical instrument accidently coming into contact with the output electrode 7 at the end of the wand 6. From the start point at zero seconds the potential at the output electrode 7 quickly ramps up to its desired maximum level of around 9 kV whilst at the same time output current sharply falls from the allowable limit of 10 µA to near zero. At 0.5 seconds the hypothetical contact between the output electrode 7 and the third party instrument, which may be deemed to have a capacitance at this point of 300 nF, causes the immediate collapse of the voltage as the electric charge is conserved but distributed between the capacitance of the active cable 5 and the capacitance of the third party instrument. The output current therefore rises to the allowable limit of 10 µA and stays there for long enough to trigger the monostable 11 to open the isolating switch 10 for 2 seconds, with zero output current from the converter 4. At the end of the 2 second duration the isolator switch 10 is re-enabled for a few tenths of a second and, again, the output current rises to the allowable limit of 10 µA for as long as the isolator switch 10 remains closed and this triggers the monostable 11 to again open the isolator switch 10, the cycle repeating for as long as the third party instrument with its 300 nF capacitance is in contact with the output electrode 7.

As will be seen from FIG. 2, for the duration of this cycle the voltage at the output electrode 7 stays low while the cumulative charge resulting from the third party contact is seen to take step-like rises every 2 seconds, reflecting the charge added to the output electrode 7 during the periods while the isolator switch 10 is closed. In the scenario depicted, shortly after 10 seconds has elapsed and during the next 2 second disable period, contact between the third party instrument and the output electrode 7 is broken, representing removal of the third party instrument from the vicinity by the surgeon upon receiving audio/visual alarm signals prompted by the micro controller 12, whereafter there is an immediate fall in charge at the output electrode 7. At the end of that particular 2 second disabled period the voltage at the output electrode 7 is seen to rise back to its operational level of about 9 kV and the current sharply falls back from 10 µA to near zero resulting in normal continuous output voltage beyond about 11 seconds from the start of the cycle. In this example, in the interest of clarity the independently variable functional current required for ionisation of the laparoscopic space between the electrode 6 and the patient P is chosen to be negligible.

Figure 3:
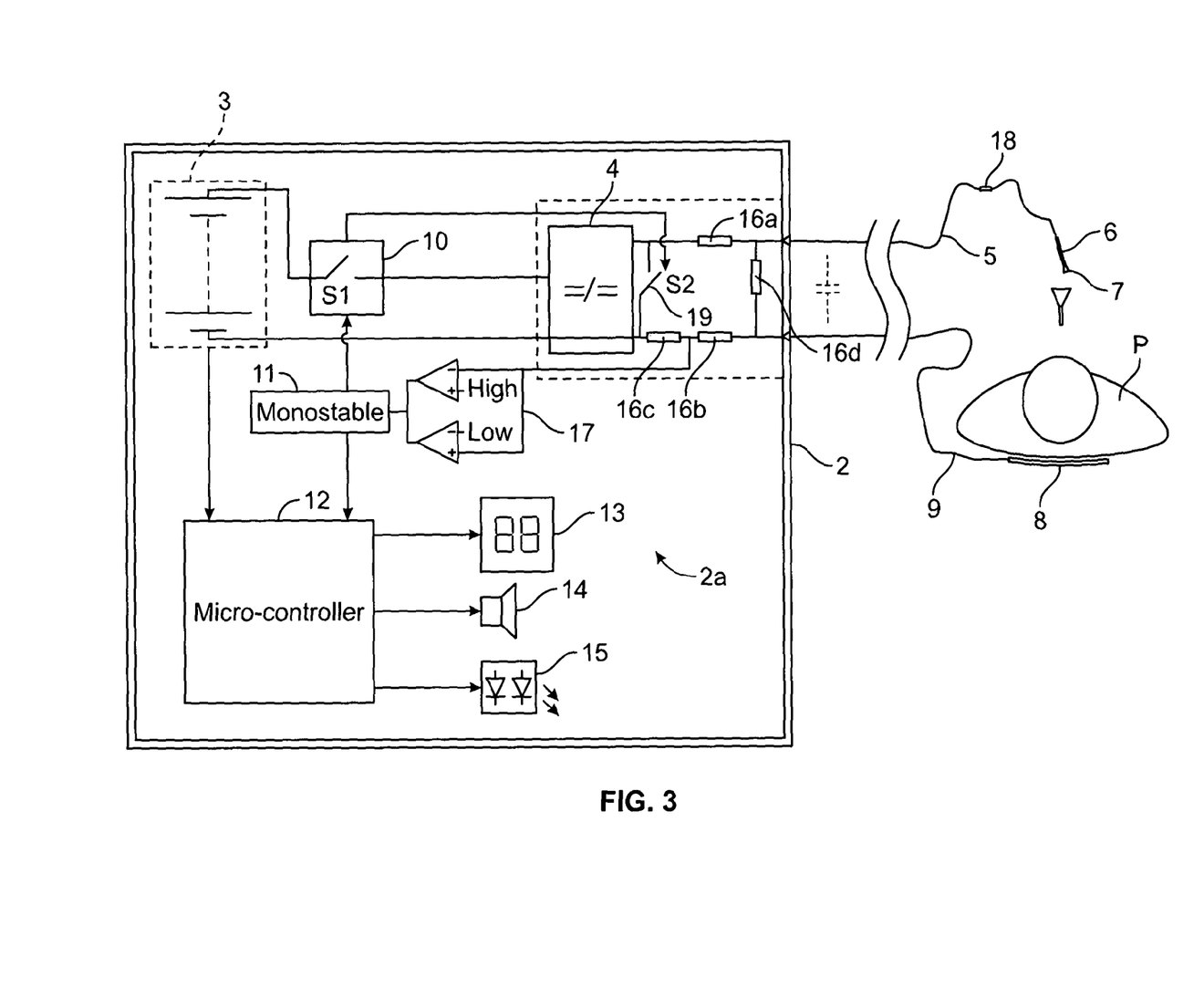
FIG. 3 is an alternative schematic arrangement to that shown with reference to FIG. 1, which includes a high voltage relay switch.

In FIG. 3 there is shown an improved safety circuit for the ionizer apparatus 1 where a high voltage relay switch 19, which may suitably be a reed type switch with normally open contacts, is positioned in shunt across the high voltage output of the converter 4. In this improved arrangement, whenever the isolator switch 10 is opened in response to an unacceptably high patient charge being detected the contact of the high voltage switch 19 is closed so as to cause a comparatively low impedance across the output and return electrodes 7, 8 and hence the patient. In this embodiment the impedance across the patient connections 7, 8 must still be low enough to avoid the risk of discharge current being drawn from a third party instrument acting as a capacitor exceeding levels deemed as likely to cause interference with the normal cardiac sinus rhythm. This is assured via the series resistors 16a, 16b as a result of the provision of the high voltage relay switch 19 which makes it is possible to establish an equilibrium condition where a charge undesirably charged to a third party instrument during periods when the isolator switch 10 is closed is withdrawn through the high voltage relay switch 19 during the periods when the isolator switch 10 is open. As a consequence, the condition where inadvertent contact is made with a third party instrument can be rendered benign, other than that during this event particle clearing is halted until the contact has been broken and normal operation of the ionizing apparatus 1 is resumed.

Figure 4:
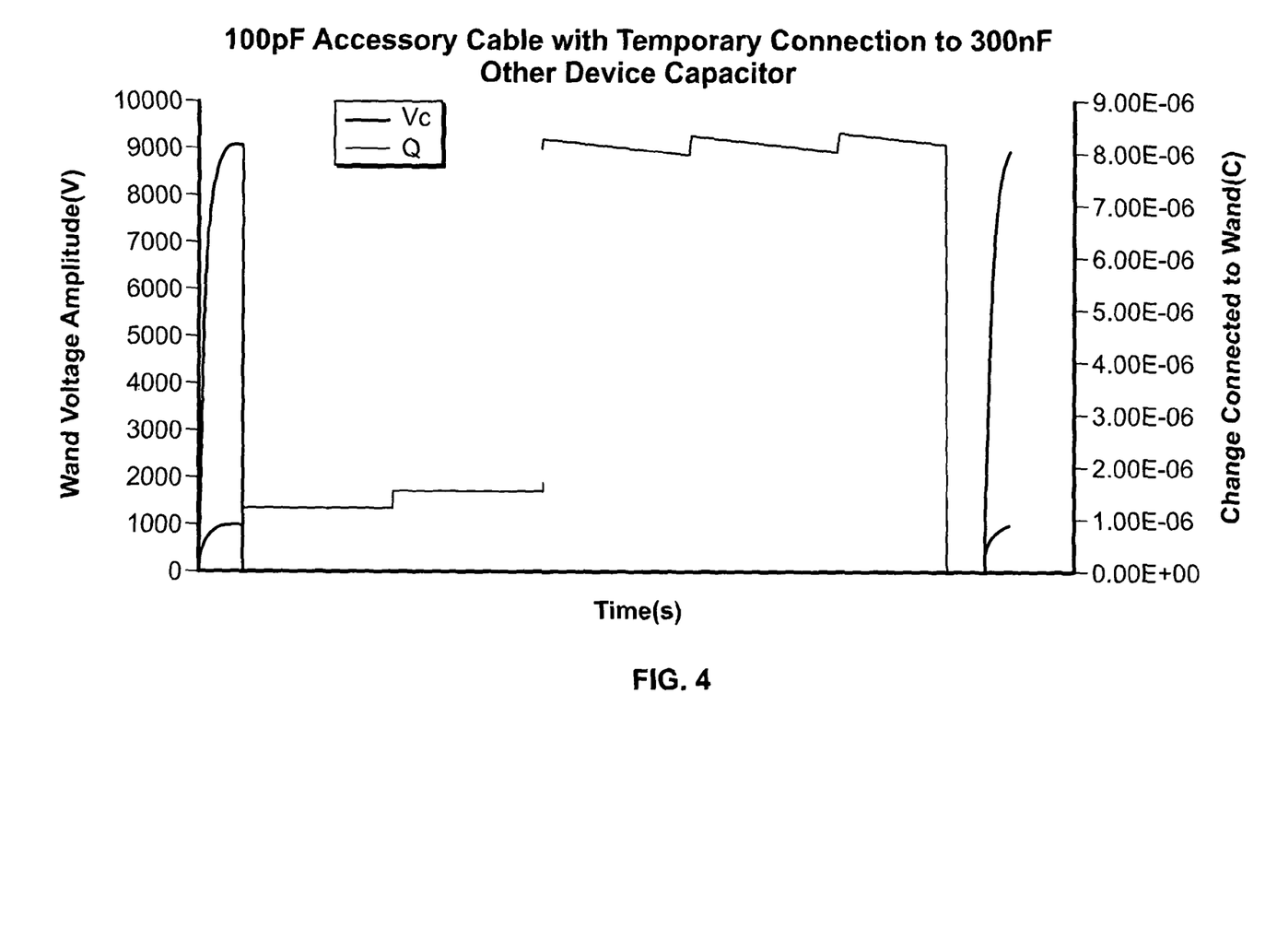
FIG. 4 is a graph showing the variation of output electrode voltage and electrical charge over time.

As with FIG. 2, FIG. 4 depicts a variation of voltage and electrical charge at the output electrode 7 over time, assuming a 1 GΩ series resistor network 16a, 16b and a 100 pF capacitance for the active cable 5 to the return electrode/pad 8. In contrast with FIG. 2, due to the discharging effect of the high voltage relay 19 shown in FIG. 3, the charge in contact with the output electrode 7 during the intermittent output period after 0.5 seconds is seen to fall back during the 2 second intervals when the isolation switch 10 is closed. The time base includes a time lapse to allow illustration of the equilibrium point being reached. The long-term outcome is that at equilibrium, the output voltage at the output electrode 7 remains low compared to the normal 9 kV level as a result of an equal charge being removed through the contacts of the high voltage relay 19 as the charge is replaced during the shorter periods when the isolation switch 10 is closed.

Figure 5:
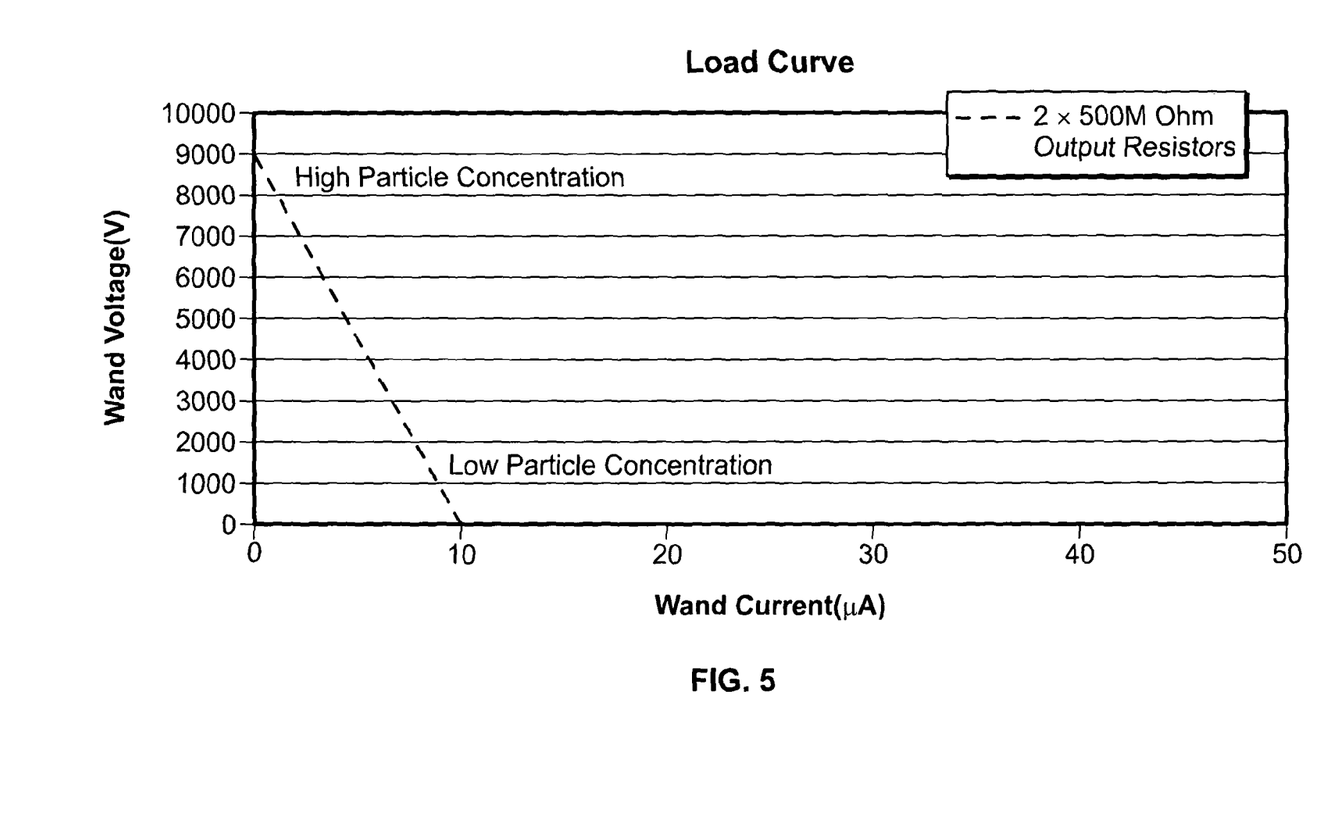
FIG. 5 shows the output voltage characteristics vs. output electrode current as they affect efficiency of particle collection.

As a result of the presence of the second current limiting means in accordance with the invention, provided by the series resistors 16a, 16b, the output voltage characteristic of the generator 8 with increasing output electrode current 7 is as shown in FIG. 5. In this example the converter 4 is set to couple 10 kV to the resistor network 16. The series resistors 16a, 16b are cumulatively set to provide 1 GΩ impedance and the shunt resistance 16d is set to 10 GΩ.

Under normal particulate-clearing operation, the impedance of the ionised pathway between the output electrode 7 and the return electrode/pad 8 is a function of the particulate type and density, the path length between the output electrode and the patient bulk tissue, and the effective surface area of the output electrode 7 and surrounding bulk patient tissue.

In practice it has been observed that a voltage of greater than 3 kV and preferably 5 kV to the output electrode 7 is required to achieve satisfactory particulate clearing, but where the output electrode 7 is placed too close to the patient bulk tissue, particulate clearing can cease as the ionised pathway impedance falls below 400 MΩ.

Where the particles to be cleared are the result of electro surgery, it has been observed that the higher ionised pathway impedances occur at higher densities of electro surgical smoke particles. As such the basic configuration depicted in FIG. 1 is optimised to offer the highest voltage between the output electrode 7 and the return electrode/pad 8 with the greatest ionising potential under conditions with the highest-particle pollution. As particle clearing completes, the ionisation pathway current between the output electrode 7 and return electrode/pad 8 is seen to rise, for example from 1.3 μA at the start of clearing to 5 μA upon completion.

Figure 6:
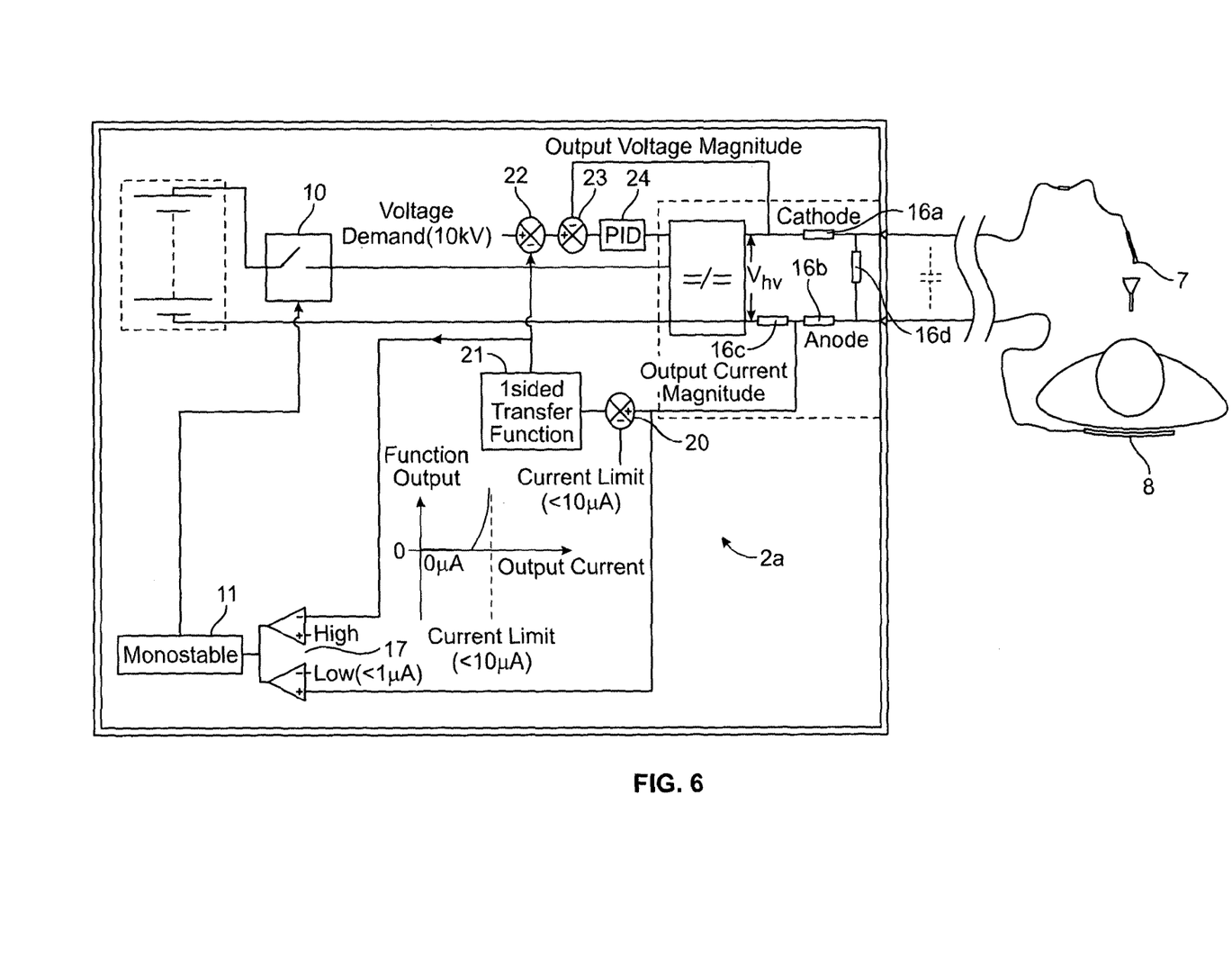
FIG. 6 is a schematic arrangement of a further embodiment of ionising apparatus and, FIG. 7 shows the ioniser load curves resulting from the embodiment shown in FIG. 6.

In FIG. 6 there is shown an improvement over the circuit described in FIG. 1 in terms of the characteristics of the output voltage of the ionising apparatus 1 with changing output current. In this case the series resistors 16 a, 16 b which ordinarily provide the second means of current limiting in the manner as described with reference to FIG. 1, are instead reduced by a factor of up to 5 so that the maximum current deliverable from the ionisation apparatus 1 under short circuit conditions rises from 10 μA towards 50 μA, governed by the relationship Vhv/(R16 a+R16 b). In lieu of the series resistors 16 a, 16 b assuring a 10 μA current limit, additional control circuitry is added, taking the current signal at the sense resistor 16 c and feeding that into a closed loop servo for rapidly reducing the voltage from the DC to DC converter 4 as the required current limit of 10 μA is approached. In this example a current summing junction 20 determines the difference between the current through the sense resistor 16 c and the allowable limit, such as 10 μA. The result is fed into a proportional-integrating-differentiating (PID) amplifier 21 with a one-sided function output, where current summing junction 20 signals indicating acceptable output current conditions this results in a zero amplitude output, but where summing junction 20 signals indicate excessive output current conditions, this results in a rapidly increasing amplitude output. This signal is fed into both the upper limit window of the window comparator 17 and into a first voltage summing junction 22 for the voltage control of the DC to DC converter 4. The polarity of signals is such that signals from the current summing junction 20 indicative of excess output current result in a reduction of output from the first voltage control summing junction 22, the output from which is then compared with the actual output voltage in a second voltage control summing junction 23. The output from the second voltage summing junction 23 is in turn fed into a second PID amplifier 24 and used to control the intensity of operation of the DC to DC converter 4 in a manner familiar to those skilled in the art.

The composite results of the current limiting provided by the series resistors 16a, 16b and the closed loop current limit circuit described above is shown in FIG. 7 where the output voltage starts at a maximum when the output electrode 7 of the return electrode 8 is zero and then falls as the output current rises, but significantly less deeply than would have been the case for the embodiment shown in FIG. 1. This is as a result of the up to 5 to 1 reduction of the values of the series resistors 16a, 16b. As impedance of the atmosphere medium between the output electrode 7 and return electrode 8 reduces further and the desired current limit, such as 10 μA, is reached, the output voltage falls asymptotically towards zero without any functionally significant increase in output current for further reductions in output electrode 7 to return electrode 8 collective impedance.

Figure 7:
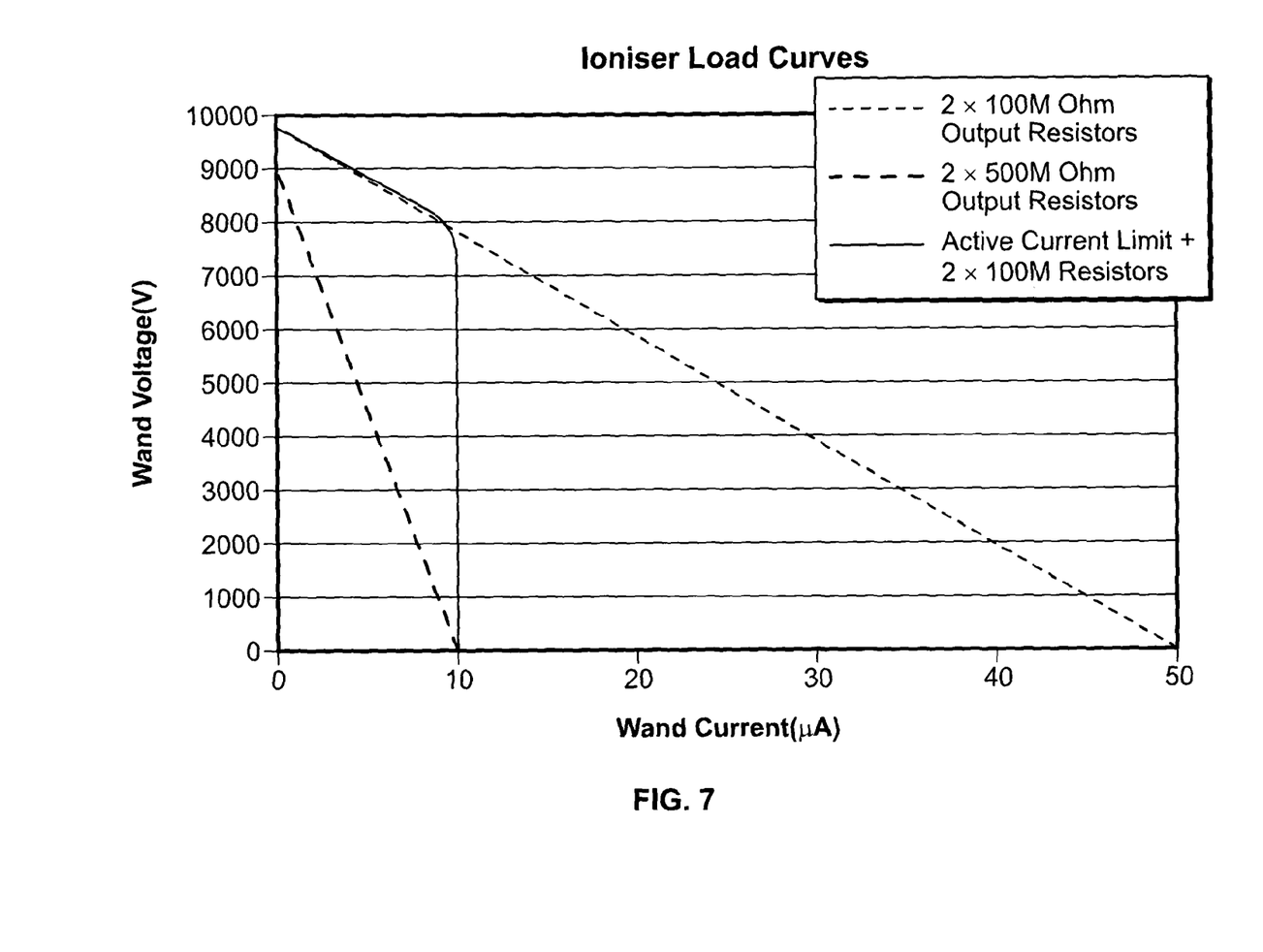

At an output voltage of approximately 3 kV or less, ionisation of the atmospheric medium between the output electrode 7 and return electrode 8 results in significantly less particulate precipitation and this condition is detected by the upper limit 17a of the window comparator 17 based on the amplitude of the signals from the first PID amplifier 21 with the one-sided output function. In a similar fashion to that implemented in the embodiment shown in FIG. 1, an out-of-range signal at the window comparator 17 results in the monostable 11 being triggered for a period of 2 to 3 seconds, during which the isolator switch 10 opens, disabling the DC to DC converter 4. In this manner an improved output voltage characteristic is achieved while output electrode 7 to return electrode 8 impedances permit an effective particulate-clearing voltage to be established between them. However, a return to intermittent operation occurs if the impedance is too low for effective particulate-clearing, or are indicative of a short circuit between the electrodes 7, 8 via human tissue or because of third party equipment capacitance.

Although several embodiments of the invention have been described it will be understood that the invention also extends to variations to these embodiments including combinations of embodiments and variations apparent to the skilled addressee.

The invention claimed is:

1. A DC driven ionisation apparatus for ionising a local atmosphere in which a corporeal surgical or cosmetic procedure is to be performed on a patient, comprising:
a power supply providing a DC voltage to a converter via an isolation switch, said converter converting the DC voltage to a high voltage DC current;
an output electrode connected to the converter and a return electrode connected to the power supply to provide an ionization path in use;

a high voltage resistor network couples the converter to the output electrode and the return electrode to the power supply, the high voltage resistor network includes a current sense resistor connected between the return electrode and the power supply for sensing a current used in detecting a hazard condition when a potential difference between the output electrode and return electrode is less than 3 kV; and a comparator to signal a monostable connected to the isolation switch to open the isolation switch for a predefined interruption duration between 2 and 3 seconds when the sensed current indicates the hazard condition;

wherein the monostable cyclically reconnects and disconnects the power supply until the hazard condition has been rectified each reconnect and disconnect cycle taking place over a period of approximately 200 ms.

2. The DC driven ionisation apparatus of claim 1, further comprising a microcontroller and at least one indicator, wherein the monostable signals the microcontroller to provide an indication of the hazard condition via the at least one indicator.

3. The DC driven ionisation apparatus of claim 2, wherein the indicator is at least one of a digital display, an audio speaker, and at least one LED.

4. The DC driven ionisation apparatus of claim 1 wherein the predefined interruption duration is between 0.2 and 10 seconds.

5. The DC driven ionisation apparatus of claim 4 wherein the monostable is arranged to attempt reconnection of the power supply, during the reconnect and disconnect cycle, for a duration less than the predefined interruption duration.

6. The DC driven ionisation apparatus of claim 1, wherein the converter includes circuitry for limiting a steady-state output current to no more than 30 microamps.

7. The DC driven ionisation apparatus of claim 1, wherein the resistor network includes a first resistor connected in series between the converter and the output electrode and a second resistor connected in series between the return electrode and the converter.

8. The DC driven ionisation apparatus of claim 7, wherein the first and second resistors each have an impedance between 0.4 and 1.2 giga-ohms.

9. The DC driven ionisation apparatus of claim 7, wherein the first resistor has an impedance between 0.4 and 1.2 giga-ohms.

10. The DC driven ionisation apparatus of claim 7, wherein the second resistor has an impedance between 0.4 and 1.2 giga-ohms.

11. The DC driven ionisation apparatus of claim 7, wherein the first and second resistors limit a steady-state output current of the converter to no more than 10 microamps.

12. The DC driven ionisation apparatus of claim 7, wherein the resistor network further includes a shunt resistor connected in parallel across the output electrode and the return electrode.

13. The DC driven ionisation apparatus of claim 7, further comprising a third resistor connected in series between the first resistor and the output electrode.

14. The DC driven ionisation apparatus of claim 13, wherein the first resistor has an impedance between 0.4 and 1.2 giga-ohms and the third resistor has an impedance of two or more orders of magnitude less than the impedance of the first resistor.

15. The DC driven ionisation apparatus of claim 13, wherein the third resistor limits peak displacement current between the output electrode and patient tissue.

16. The DC driven ionisation apparatus of claim 1, further comprising a high voltage switch connected in parallel across an output of the converter.

17. The DC driven ionization apparatus of claim 16, wherein the high voltage switch is normally open and the comparator further signals the high voltage switch to close when the comparator signals the monostable to open the isolation switch for the predefined interruption duration.

18. The DC driven ionization apparatus of claim 7, wherein the first and second resistors limit a steady-state output current of the converter to no more than 50 microamps, and further comprising a closed loop current limit circuit for reducing the output voltage of the converter.

19. The DC driven ionization apparatus of claim 18, wherein the closed loop current limit circuit includes a current summer that outputs a difference of the sensed current and a threshold current to an amplifier, said amplifier having a zero output when the current summer output indicates acceptable conditions and an increasing amplitude output when the current summer output indicates excessive output current conditions, the amplifier output is fed to the comparator and a first voltage summer, the first voltage summer receives a voltage demand signal which is reduced by the amplifier output, an output of the first voltage summer is fed to a second voltage summer that outputs a difference of the output of the first voltage summer and a sensed converter output voltage, an output of the second voltage summer is fed to a second amplifier which provides a voltage control signal to the converter.

20. A DC driven ionisation apparatus for ionising a local atmosphere in which a corporeal surgical or cosmetic procedure is to be performed on a patient, comprising:

a power supply providing a DC voltage to a converter via an isolation switch, said converter converting the DC voltage to a high voltage DC current;

an output electrode connected to the converter and a return electrode connected to the power supply to provide an ionization path in use;

a high voltage resistor network couples the converter to the output electrode and the return electrode to the power supply, the high voltage resistor network includes a current sense resistor connected between the return electrode and the power supply for sensing a current used in detecting a hazard condition; and a comparator to signal a monostable connected to the isolation switch to open the isolation switch for a predefined interruption duration when the sensed current indicates the hazard condition;

wherein the monostable cyclically reconnects and disconnects the power supply until the hazard condition has been rectified, wherein the resistor network includes a first resistor connected in series between the converter and the output electrode and a second resistor connected in series between the return electrode and the converter, wherein the first and second resistors limit a steady-state output current of the converter to no more than 50 microamps, and further comprising a closed loop current limit circuit for reducing the output voltage of the converter, and wherein the closed loop current limit circuit includes a current summer that outputs a difference of the sensed current and a threshold current to an amplifier, said amplifier having a zero output when the current summer output indicates acceptable conditions and an increasing amplitude output when the current summer output indicates excessive output current conditions, the amplifier output is fed to the comparator and a first voltage summer, the first voltage summer receives a voltage demand signal which is reduced by the amplifier output, an output of the first voltage summer is fed to a second voltage summer that outputs a difference of the output of the first voltage summer and a sensed converter output voltage, an output of the second voltage summer is fed to a second amplifier which provides a voltage control signal to the converter.

* * * * *